(12) United States Patent
Brass (10) Patent No.: US 12,290,147 B2
(45) Date of Patent: May 6, 2025

(54) FOOTWEAR FOR PREVENTING OR TREATING A PATHOLOGICAL DEFORMITY OF A WEARER'S FOOT

(71) Applicant: Hallufix AG, Grünwald (DE)

(72) Inventor: Manfred Brass, Grünwald (DE)

(73) Assignee: Hallufix AG, Grünwald (DE)

( * ) Notice: Subject to any disclaimer, the term of this patent is extended or adjusted under 35 U.S.C. 154(b) by 141 days.

(21) Appl. No.: 17/912,759

(22) PCT Filed: Mar. 22, 2021

(86) PCT No.: PCT/EP2021/057323
§ 371 (c)(1),
(2) Date: Sep. 19, 2022

(87) PCT Pub. No.: WO2021/186084
PCT Pub. Date: Sep. 23, 2021

(65) Prior Publication Data
US 2023/0147885 A1    May 11, 2023

(30) Foreign Application Priority Data
Mar. 20, 2020   (DE) .......................... 102020107801.3

(51) Int. Cl.
*A43B 7/26*     (2006.01)
*A43B 3/12*     (2006.01)
(Continued)

(52) U.S. Cl.
CPC ................ *A43B 7/26* (2013.01); *A43B 3/126* (2013.01); *A43B 7/1495* (2013.01); *A43C 11/165* (2013.01); *A61F 5/019* (2013.01)

(58) Field of Classification Search
None
See application file for complete search history.

(56) References Cited

U.S. PATENT DOCUMENTS 3,066,678 A * 12/1962 Riecken ................... A43B 7/26
                                                            D2/918
3,275,002 A *  9/1966 Scholl ..................... A43B 3/126
                                                            36/11.5
(Continued)

FOREIGN PATENT DOCUMENTS

DE          1261778 A       2/1968
GB          1065392 A       4/1967
(Continued)

OTHER PUBLICATIONS

German Search Report issued for the corresponding German application DE10 2020 107 801.3, 10 pages, dated Oct. 13, 2020.
(Continued)

*Primary Examiner* — Jila M Mohandesi
(74) *Attorney, Agent, or Firm* — Ruggiero McAllister & McMahon LLC (57) ABSTRACT

A footwear is provided for preventing or treating a pathological deformity of a wearers foot, comprising a toe strap for being fastened to the great toe, an upper for being fastened to a metatarsus region of the foot and comprising a lateral section and a medial section, and an adjustment mechanism comprising a tension element coupled to the toe strap and configured for variably adjusting a pulling force applied to the toe strap, wherein the adjustment mechanism is arranged in or on the lateral section of the upper such that the tension element is guided to a lateral side of the footwear. The medial section of the upper extends from the adjustment mechanism in a medial direction to a medial side of the footwear and is adjustable in its circumferential length.

19 Claims, 2 Drawing Sheets

(51) Int. Cl.
*A43B 7/14* (2022.01)
*A43C 11/16* (2006.01)
*A61F 5/01* (2006.01)

(56) References Cited

U.S. PATENT DOCUMENTS

| | | | | |
|---|---|---|---|---|
| 4,200,997 | A * | 5/1980 | Scheinhaus | A43C 11/1493 36/11.5 |
| 4,300,294 | A * | 11/1981 | Riecken | A43B 3/24 36/97 |
| 4,632,103 | A * | 12/1986 | Fabricant | A61F 5/019 602/30 |
| 4,719,670 | A * | 1/1988 | Kurt | A43B 5/04 242/395 |
| 4,813,162 | A * | 3/1989 | Harris | A43B 3/108 36/43 |
| 4,937,953 | A | 7/1990 | Walkhoff | |
| 5,181,331 | A * | 1/1993 | Berger | A43C 11/00 24/712.1 |
| 6,202,325 | B1 * | 3/2001 | Kim | A43B 3/105 D2/959 |
| 7,134,224 | B2 * | 11/2006 | Elkington | A43B 5/0401 36/50.1 |
| 7,794,417 | B1 | 9/2010 | Zimmerman | |
| 10,195,068 | B2 * | 2/2019 | Wiley | A61F 5/0111 |
| D977,800 | S * | 2/2023 | McClaskie | D2/917 |
| 2007/0074334 | A1 * | 4/2007 | Steel | A41B 11/004 36/9 R |
| 2011/0061262 | A1 * | 3/2011 | Krauss | A61F 5/14 36/43 |
| 2016/0242508 | A1 * | 8/2016 | Heid | A43B 7/147 |
| 2019/0350304 | A1 * | 11/2019 | Velazquez | A43B 5/00 |
| 2020/0229531 | A1 * | 7/2020 | Driscoll | A43B 3/122 |
| 2020/0383813 | A1 | 12/2020 | Brass et al. | |

FOREIGN PATENT DOCUMENTS

| | | |
|---|---|---|
| JP | S62-114502 A | 5/1987 |
| JP | H01148201 A | 6/1989 |
| KR | 102007740 B1 | 8/2019 |
| WO | 2012028921 A1 | 3/2012 |
| WO | 2019102033 A1 | 5/2019 |

OTHER PUBLICATIONS

International Search Report and Written Opinion for corresponding International (PCT) application PCT/EP2021/057323, 12 pages, dated May 27, 2021.

Japanese Office Action for the corresponding Japanese application 2022-556693, 5 pages, dated Jul. 23, 2024.

* cited by examiner

FOOTWEAR FOR PREVENTING OR TREATING A PATHOLOGICAL DEFORMITY OF A WEARER'S FOOT

CROSS REFERENCE TO RELATED APPLICATIONS

This application is a national stage U.S. patent application of International Application No. PCT/EP2021/057323, filed on May 27, 2021, and claims foreign priority to German Patent Application No. DE 10 2020 107 801.3, filed on Mar. 20, 2020 the entirety of each of which is incorporated herein by reference.

TECHNICAL FIELD

Footwear for preventing or treating a pathological deformity of a wearer's foot in the metatarsal and forefoot region, such as a joint connecting the great toe to the foot, e.g. which may be referred to as hallux valgus or bunion.

TECHNOLOGICAL BACKGROUND

Deformity or malposition in the metatarsal and forefoot region, particularly a pathological skew condition of the great toes that is referred to as hallux valgus, may be caused by different factors. For example, such pathological deformities may be caused by genetic predisposition, wearing incorrect footwear, in particular overly tight or heeled shoes, or flattening of the longitudinal and transverse arch as a result of instability in the metatarsal region, particularly due to an instability of the connective tissue. As a result of the flattening of the transverse arch, which is also referred to as splayfoot, the individual metatarsal and toe bones are fanned out radially. The metatarsal bone of the first ray, i.e. the inner or medial metatarsal bone, is abducted inwardly. As a result, the tendons of the great toe which, unlike the other toes, has an independent tendon apparatus, no longer run centrally over the first metatarsophalangeal joint but, due to their predefined length, laterally outside thereof. The great toe is thus pulled into an oblique and outwardly oriented position. To that end, the formation of hallux valgus is amplified by the subsidence of the longitudinal arch, because this predominantly medial subsidence results anatomically in an outward rotation of the metatarsus and forefoot when seen from above.

From the prior art, the use of therapeutic footwear is known to prevent or treat hallux valgus diseases of the wearer's foot. US 2016/0242508 A1, for example, discloses a therapeutic sandal configured for repositioning the wearer's great toe to decrease pressure on the first metatarsalphalangeal joint. For doing so, the sandal comprises a sole through which an adjustable strap is movably guided from a medial side to a lateral side of the sandal. A toe section of the strap protrudes from the medial side and is fastened to the sole so as to form a loop for receiving the great toe of the wearer. To that end, a metatarsus section of the strap protrudes from the lateral side of the sole and is fastened to a slot at the medial side for holding a metatarsus region of the wearer's foot between the metatarsus section of the strap and the sole. An end portion of the metatarsus section is guided through the slot at the medial side of the sole and coupled to an upper surface of a middle portion of the metatarsus section by means of a Velcro connection over the top of the wearer's foot. In this way, the length of the strap is adjustable. Specifically, by such a configuration, a therapeutic force exerted on the great toe can be adjusted upon tightening the strap. However, by doing so, i.e. by shortening the effective length of the strap, the metatarsus section around the metatarsus region of the foot and the toe section of the strap are simultaneously tighten.

Thus, in the known therapeutic footwear, built up or adjustment of holding forces applied to the metatarsus region of the foot and therapeutic forces applied to the great toe are directly coupled to one another, i.e. cannot be adjusted independently from one another. However, this may affect proper fixation of the footwear to the wearer's foot and/or proper adjustment of a therapeutic force to be exerted onto the wearer's foot.

SUMMARY

Described are exemplary embodiments of footwear for preventing or treating a pathological deformity of a wearer's foot, such as of a joint connecting a great toe to the foot, which particularly enables to more effectively and accurately fasten or adjust the footwear to a wearer's foot.

Accordingly, a footwear for preventing or treating a pathological deformity of a wearer's foot, in particular of a joint connecting a great toe to the foot, is provided. The proposed footwear comprises a toe strap configured for being fastened to the great toe, an upper configured for being fastened to a metatarsus region of the foot and comprising a lateral section and a medial section, and an adjustment mechanism comprising a tension element coupled to the toe strap and configured for variably adjusting a pulling force applied to the toe strap which, in a fastened state in which the footwear is fastened to the foot, is translated into a corrective force acting upon at least one of the joint and the great toe. The adjustment mechanism is at least partially arranged in or on the lateral section of the upper such that the tension element is guided to a lateral side of the footwear. The medial section of the upper extends from the adjustment mechanism in a medial direction to a medial side of the footwear and is adjustable in its circumferential length.

The proposed footwear may be used for prevention or treatment of a pathological deformity or malposition of a wearer's or patient's foot. Specifically, the proposed footwear may be used to prevent or treat hallux valgus or bunion diseases, but is not limited to this application. Hallux valgus or bunion diseases typically refer to a pathological deformity or malposition of a joint connecting a great toe to the foot of a patient, also referred to as the "great toe joint" in the following. Accordingly, the proposed footwear may be used for prevention or treatment of deformity or malposition of the wearer's great toe joint.

For preventing or treating the aforementioned pathological deformity of the wearer's or patient's foot, also referred to as the foot in the following, the proposed footwear is configured and designed to exert a corrective force to the foot in the fastened state of the footwear, i.e. when being fastened to the foot. Specifically, the corrective force is intended to force those parts of the foot subjected to the pathological deformity into an anatomically correct or intended position to achieve a desired therapeutic effect. A detailed description of the corrective forces applied to the wearer's foot and the therapeutic effects interlinked therewith are set forth below in connection with the description of components of the footwear associated thereto.

The proposed footwear, as set forth above, is configured and designed for being fastened, i.e. releasably fastened, to a patient's foot. In the context of the present disclosure, the term "footwear" refers to any garment, in particular shoe, intended for being fastened to a patient's foot in a predefined position and orientation relative to the foot. Specifically, the footwear may be provided in the form of any type of shoe, for example, a closed shoe or an opened shoe, such as a sandal. To that end, the footwear may be provided in the form of a splint.

The footwear may comprise a base or sole configured to receive a bottom or sole of the foot. In other words, in the fastened state of the footwear, the bottom of the foot may be in contact with the sole. Further, the sole may be designed to provide the footwear with certain structural stability and wear resistance, i.e. to receive and absorb forces during use of the footwear. Thus, compared to other components of the footwear, the sole may be provided with higher mechanical strength, resistance and rigidity. The sole may be provided as an integral part or as a multi-piece part. Specifically, the sole may be provided with a multi-layer design which may comprise at least two layers, in particular horizontal layers. For example, the sole may comprise a layer structure comprising at least two of an outsole, a midsole, an insole and an inserted sole. The sole may be made of any suitable material or a mixture of different materials.

As set forth above, the footwear comprises the toe strap which is configured for being fastened to a great toe of the foot, also referred to as the first toe, the big toe, the innermost toe or hallux. In other words, in the fastened state of the footwear, the toe strap may be designed and configured to hold and fix the great toe in a predefined position within the footwear, in particular relative to the sole. For doing so, the toe strap may be secured or fastened, particularly fixedly fastened, to the sole.

Specifically, the toe strap may comprise a first end fixed to the sole. The toe strap may be provided such that, in the fastened state of the footwear, the first end is arranged between the great toe and the second toe of the foot. According to one configuration, the first end of the toe strap may at least partly intrude into the sole and optionally may be arranged between different layers of the sole. In this way, a particularly firm connection between the sole and the toe strap may be provided.

Further, the toe strap may comprise a second end which is arranged on an opposed side compared to the first end. The second end may be fastened to the tension element of the adjustment mechanism. According to one configuration, the second end of the toe strap may be releasably fastened to the tension element. In this way, a connection between the second end of the toe strap and the tension element may be selectively engaged and disengaged. By allowing that the second end of the toe strap may be released from the tension element, the footwear may allow to remove and exchange an upper layer of the sole, i.e. the insole or the inserted sole. This may be achieved by a sole which is provided with a through opening in its upper layer through which the toe strap, i.e. its first end is guided. By releasing the second end to be exposed from any other component of the footwear, the upper sole may be released from the sole and moved relative to the toe strap such that the toe strap is pulled out from the through opening in the upper layer, thereby structurally decoupling the upper layer from the footwear.

The toe strap may be provided such that the first end of the toe strap is arranged in front of the second end of the toe strap in a forward direction of the footwear, i.e. a direction pointing from a heel of the foot towards its toes.

The toe strap may be provided with a longitudinal shape, i.e. having a length that is substantially greater than a width thereof. Additionally, the strap may be provided with a flat shape, having a thickness that is substantially smaller than the length and the width thereof. The toe strap may be fastened to the sole such that, in the region of its first end, the toe strap is arranged parallel to the forward direction of the footwear. In other words, in the region of its first end, the toe strap may be arranged such that its width direction points into a direction that is substantially parallel to the forward direction of the footwear. In this way, the wear comfort of the footwear may be improved.

The toe strap may be configured and designed to be arranged circumferentially around the great toe when the footwear is in its fastened state. In this configuration, the footwear may be provided such that, upon exerting the pulling force to the toe strap, in particular its second end, via the tension element, a wrap length of the toe strap around the great toe may be adjusted. In other words, by applying the pulling force to the toe strap, a wrap length of the toe strap around the great toe may be decreased. By doing so, the pulling force may be translated into the corrective force acting upon the great toe such that the great toe is moved or tensioned into a medial direction. As a result, the great toe is subjected to a therapeutic force, thereby being forced into an anatomically correct or desired position so as to prevent or treat the pathological deformity of the foot.

In a further development, the footwear may be provided such that the toe strap is designed and configured to, in the fastened state of the footwear, be spanned from its first end via the great toe to a medial side of the footwear. Specifically, the toe strap may be spanned such that it extends along the outer surface of the foot, in particular the great toe, from a lateral side of the toe to a medial side of the toe and/or the great toe joint. In this configuration, the toe strap, in particular a longitudinal axis thereof, may extend along the outer surface of the great toe in a medial direction and a backward direction of the footwear, i.e. pointing from the toes towards the heel of the foot. In other words, according to this configuration, the toe strap, in particular its longitudinal axis, may extend backwardly and medially inclined, i.e. in the medial and backward direction, along the outer surface of the great toe. In this way, the toe strap, in particular its longitudinal axis, may have a helical shape.

Further, the toe strap may be provided with a seat surface configured to, in the fastened state of the footwear, contact and fit against the outer surface of the foot, i.e. against at least one of the great toe and the joint connecting the great toe to the foot. Optionally, in the fastened state of the footwear, between the outer surface of the foot and the seat surface, other parts of the footwear, e.g. parts of the upper, such as the medial section, may be arranged. Specifically, the seat surface may be provided with a first effective surface arranged at or in the region of the lateral side of the great toe and a second effective surface arranged at or in the region of the medial side of the great toe or the great toe joint in the fastened state of the footwear. In this configuration, upon applying the pulling force to the toe strap, the first effective surface may apply a first corrective force to the lateral side of the great toe which moves and/or tensions the great toe into a medial direction. To that end, upon applying the pulling force to the toe strap, the second effective surface may apply a second corrective force to the medial side of the great toe and/or the great toe joint which moves and/or tensions the joint into a lateral direction. As a result, both the great toe and the joint are subjected to a therapeutic force, thereby being forced into an anatomically correct or desired position. In this way, a particularly effective therapeutic treatment or prevention of hallux valgus diseases may be provided.

Further, as set forth above, the footwear comprises the upper configured for being fastened to a metatarsus region of the foot. In the context of the present disclosure, the term "upper" refers to a s part of the footwear which is configured to hold the foot in a desired position and orientation within the footwear. According to one configuration, for example when the footwear is provided in the form of an open shoe such as a sandal, the upper may be constituted by one or more straps extending over the metatarsus region of the foot. In the fastened state of the footwear, the upper may be designed and configured to hold and fix the metatarsus region of the foot in a predefined position within the footwear, in particular relative to the sole. For doing so, the upper may be secured or fastened, particularly fixedly fastened, to the sole. Specifically, at least one of, e.g. both, the lateral section and the medial section of the upper may be fastened or fixed to the sole. Specifically, a lateral end of the lateral section may be fastened or fixed, particularly directly fastened or fixed, to the sole. Alternatively or additionally, a medial end of the medial section may be fastened or fixed to the sole, in particular directly fastened or fixed to the sole.

In the proposed footwear, as set forth above, the upper comprises the lateral section and the medial section. In the context of the present disclosure, the lateral section and the medial section refer to distinct and delimited sections of the upper, wherein along a boundary between the sections, the lateral section extends therefrom in the lateral direction and the medial section extends therefrom in the medial direction.

Specifically, the lateral section is provided and intended to carry or accommodate the adjustment mechanism, in particular at least a part thereof. Accordingly, the adjustment mechanism may be arranged on or in the lateral section of the upper such that it is arranged laterally, i.e. in a lateral direction, from the boundary extending between the lateral section and medial section of the upper.

To that end, in the proposed footwear, the medial section may refer to a part of the upper which extends from the adjustment mechanism in a medial direction to a medial side of the footwear. In other words, the medial section may be arranged adjacent to or apart from the adjustment mechanism. Accordingly, the medial section may refer to a part of the upper which is not in direct contact to the adjustment mechanism.

In the following, the operation and structural configuration of the adjustment mechanism is further specified.

The adjustment mechanism is designed and configured to variably adjust the pulling force applied to the toe strap which, in the fastened state of the footwear, is translated into the corrective force acting upon at least one of the great toe and joint connecting the great toe to the foot. In other words, the adjustment mechanism is accordingly designed and configured to variably set a corrective force to be applied to at least one of the great toe or joint connecting the great toe to the foot. For doing so, the adjustment mechanism comprises the tension element which is connected to the toe strap.

In the context of the present disclosure, the term "adjustment mechanism" may refer to a component of the footwear which is configured for tightening and/or untightening the toe strap and which may be arranged on the lateral section of the upper. Further, the term "tension element" refers to a component, i.e. flexible component, such as a rope or wire, which is designed and configured to transmit a tensioning force to the toe strap, in particular its second end. In other words, the tension element may be a tension-resistant wire which force-fittingly connects the toe strap to the adjustment mechanism.

For being capable of applying the pulling force to the toe strap, the footwear may be provided such that the tension element is movably guided within the footwear. Specifically, the tension element may be supported within the footwear such that it is movable along its longitudinal axis so as to pull the toe strap, in particular its second end, thereby applying the pulling force.

As set forth above, the lateral section is intended and configured to guide the tension element of the adjustment mechanism to a lateral side of the footwear. Further, the adjustment mechanism and the lateral section of the upper may be designed and provided such that the tension element is guided into the sole of the footwear. For example, the tension element may be supported along the lateral side of the footwear such that it is guided into the sole of the footwear from a lateral side or outer side of the footwear. Specifically, the tension element may be supported or guided in or on the lateral section of the upper such that the tension element is translationally movable relative to the lateral section along the longitudinal axis of the tension element.

To that end, the tension element may be supported or guided in or on the sole of the footwear such that the tension element is translationally movable relative to the sole along the longitudinal axis of the tension element. Additionally or alternatively, the toe strap may be supported or guided in or on the sole of the footwear such that the toe strap is translationally movable relative to the sole along the longitudinal axis of the tension element. In this configuration, a coupling for connecting the tension element to the toe strap may be arranged in or on the sole and, upon actuation of the toe strap, i.e. when being subjected to the pulling force, may be configured to translationally move relative to the sole in the longitudinal axis of the tension element and the toe strap. Alternatively, the coupling for connecting the tension element to the toe strap may be arranged on a lateral side of the footwear, in or on the lateral section of the upper or on a medial side of the footwear, in particular a medial outer side of the footwear.

For doing so, the sole may be provided with a channel for receiving and guiding at least one of the tension element and the toe strap. By this configuration, the tension element and/or the toe strap may be supported in the sole such that they/it are/is translationally movable relative to the sole along a longitudinal axis of the channel. In this configuration, the longitudinal axis of the channel may coincide or be parallel to the longitudinal axis of a portion of the tension element and/or the toe strap which is arranged within the channel.

Specifically, the channel may be provided such that it, i.e. its longitudinal axis, extends through the sole from a medial side to a lateral side of the footwear in the lateral and backward direction of the footwear. In other words, the channel, i.e. its longitudinal axis, may extend backwardly and laterally inclined from a medial side to a lateral side of the footwear. Further, the channel may be provided in the sole such that, in the fastened state of the footwear, the channel is arranged after the great toe joint or a great toe ball in the backward direction of the footwear.

The sole may be designed such that the tension element is guided through one of its layers or between two of its layers. Accordingly, the channel for supporting and guiding the tension element and/or the toe strap may be provided so as to run through one of the sole layers or elements or between two of its sole layers or elements. For example, the tension element may be guided through the outsole or between the outsole and the insole or between the insole and the inserted sole.

Further, for actuating the tension element, in particular for tightening or untightening, the adjustment mechanism further comprises an adjustment unit. The adjustment mechanism may be provided such that the tension element may be translationally moved relative to the adjustment unit, in particular along its longitudinal axis, so as to variedly adjust the pulling force applied to the toe strap. Additionally, the adjustment mechanism may be configured such that the translational movement between the adjustment unit and the tension element, in particular along the longitudinal axis of the tension element, can be selectively locked so as to set and maintain a desired pulling force to be applied to the toe strap. The adjustment unit may be configured to selectively release, i.e. allow, or lock a relative translational movement between the tension element and the adjustment unit along the axial direction of the tension element so as to variedly adjust and set the pulling force applied to the toe strap. In other words, the adjustment unit may be configured to selectively engage or disengage a force-fitting coupling between the adjustment unit and the tension element.

In a further development, the adjustment unit may be operated in a tightening or untightening operating mode in which relative translational movement between the adjustment unit and the tension element along its longitudinal axis is allowed. Further, the adjustment unit may be operated in a secured operating mode in which relative translational movement between the adjustment unit and the tension element along its longitudinal axis is secured or locked. The adjustment unit may be configured to switch from the secured operating mode into the tightening or untightening operating mode when an actuation force applied to the adjustment unit by a user exceeds a threshold value.

According to one configuration, the adjustment unit may comprise a rotatably actuatable element, in particular a rotary knob, wherein the adjustment unit is configured to translate a rotational movement of the rotatably actuatable element into a translational movement of the tension element relative to the adjustment unit along the longitudinal axis of the tension element. For example, the adjustment unit may be configured such that a rotational movement of the rotatably actuatable element into a first direction causes tightening of the tension element and a rotational movement of the rotatably actuatable element into a second opposed direction causes untightening of the tension element. Wherein tightening of the tension element may be performed by pulling or retracting the tension element into the adjustment unit and untightening may be performed by pulling the tension element out of the adjustment unit.

According to one configuration, the tension element may be provided in the form of a lace, wherein the adjustment unit may be constituted by an end portion of the lace, in particular a lateral end section, and lace eyelets provided in the lateral section of the upper. Specifically, the lace eyelets may be designed and provided such that the end portion of the lace may be passed through the lace eyelets and may be moved relative to the lace eyelet in the longitudinal axis of the lace and the lace eyelet so as to tighten or untighten the adjustment mechanism. Further, the adjustment unit may be designed and provided such that the lace can be secured to the lace eyelet, e.g. by means of a shoe-tying knot, so as to lock relative movement between the lace and the lace eyelet along the longitudinal axis, in particular in at least one direction along the longitudinal axis.

According to one configuration, the tension element may be provided, at least partially, e.g. at a lateral end portion thereof, in the form of a strap, wherein the adjustment unit may be constituted by a Velcro connection between the tension element, i.e. its lateral end portion, and the lateral section of the upper. By such a configuration, the tension element may be releasably and adjustably fastened to the adjustment unit, i.e. the lateral section of the upper. Accordingly, for tightening or untightening the tension element in order to variedly adjust the pulling force to be applied to the toe strap, the Velcro connection may be released such that the tension element may be moved relative to the adjustment unit, i.e. along its longitudinal axis. After a desired pulling force is adjusted, the Velcro connection may be engaged by fitting the lateral end portion of the tension element tightly to the upper surface of the lateral section of the upper. In this way, relative translational movement between the tension element and the adjustment unit may be locked.

It will be obvious for a person skilled in the art that the proposed footwear is not limited to the above described configurations of the adjustment mechanism. Rather, any suitable fastening means may be used as an adjustment mechanism in the sense of the present disclosure which is suitable for selectively locking or releasing relative translational movement of the tension element relative to the lateral section of the upper along the longitudinal axis of a part of the tension element which is arranged on or in the lateral section of the upper.

As set forth above, the medial section refers to a part of the upper which extends from the adjustment mechanism in a medial direction to a medial side of the footwear. Thus, in the fastened state of the footwear, the medial section is configured to lie upon or be arranged on the metatarsus region of the foot so as to hold the footwear in a desired position and orientation on the foot.

Further, the medial section is designed such that it is adjustable, i.e. variably adjustable in its circumferential length. In the context of the present disclosure, the term "circumferential" or "circumferential length" refers to a perimeter or extent direction of the medial section which defines a path along the metatarsus region of the foot between a lateral side and medial side of the footwear.

By being variably adjustable in its circumferential length, the medial section may ensure proper adjustment of the upper relative to a foot to be received in the footwear. In this way, the footwear, i.e. its shape, may be purposefully adapted to different foot shapes and thus provides the footwear with a certain degree of configurability. As a result, proper fitting of the footwear to different foot types and foot shapes may be ensured.

The medial section may be configured such that it is adjustable in its circumferential length independently from an actuation of the adjustment mechanism. Specifically, the medial section may be configured such a circumferential length thereof can be increased or decreased independently from an actuation of the adjustment mechanism. For example, when the adjustment mechanism is in a released state, in which toe strap and thus the tension element is not subjected to the pulling force, the medial section is adjustable in its circumferential length independently from an actuation of the adjustment mechanism, i.e. independently from or without tightening or untightening the tension element and/or the toe strap. In other words, in the fastened state of the footwear, the medial section may be subjected to a tensile force for holding the foot, i.e. its metatarsus region relative to the footwear, which may be adjusted or applied independently from the pulling force applied to the toe strap.

In the proposed footwear, since the adjustment mechanism is received in or on the lateral section and the medial section extends from the adjustment mechanism in a medial direction to the medial side of the footwear, the medial section and the adjustment mechanism may be spatially separated from one another. By such a configuration, the proposed footwear may be provided with the advantageous effect of enabling that adjustment of the pulling force to be applied to the toe strap may be performed decoupled from adjustment of a circumferential length of the medial section of the upper, and vice versa. Accordingly, a user may separately actuate the adjustment mechanism for setting the pulling force and a further adjustment mechanism, e.g. provided on or in the medial section of the upper, for setting a circumferential length of the upper, i.e. its medial section. In this way, i.e. by providing such decoupled and selective adjustments, the proposed footwear allows for more accurately adjust, i.e. with more degrees of freedom, the footwear to the wearer's foot. Compared to known footwear or therapeutic shoes, the proposed solution enables to more accurately adjust a desired therapeutic force or effect to be applied and, at the same time, may increase usability and wear comfort of the footwear, thereby improving treatment acceptance of the wearer.

For example, improved usability of the footwear may be achieved since a wearer may more pleasantly and comfortably fastened the proposed footwear to its foot. Specifically, in a first step, the wearer may place its foot into the footwear and thereafter adjust a circumferential length of the upper, i.e. its medial section, so as to properly fix the footwear to the foot without simultaneously applying a pulling force to the toe strap or the corrective force to the great toe. During this first adjustment, the user may ensure that the footwear is held application-specifically and comfortably at the foot. Then, after the foot is hold in a desired position and orientation in the footwear, in a next step, the user may actuate the adjustment mechanism so as to apply the pulling force to the toe strap and thus to set the desired or therapeutic force to the great toe or the joint connecting the great toe to the foot. By this approach, application of the desired corrective or therapeutic force may be more accurately applied since, during building up of the corrective or therapeutic force to be applied to the great toe or its joint, the foot, i.e. the metatarsus region of the foot, may be already held in a desired or predefined position and orientation. In this way, it may be prevented that, upon building up the corrective or therapeutic force by actuating the adjustment mechanism, the foot, i.e. its metatarsus region, is unintendedly moved, thereby affecting the desired therapeutic effect to be achieved.

In order for being adjustable in its circumferential length, the medial section may be provided with a fastening means which is configured to connect two opposing portions of the medial section. The two opposing portions may be provided so as to face one another. Further, the two opposing portions may be provided so as to be movable relative to one another in a circumferential direction. In other words, upon increasing or decreasing a distance between the two opposing portions of the medial section, the circumferential length of the upper, i.e. its medial section, may be increased or decreased. In this configuration, the fastening means may be configured to connect, i.e. tension-resistantly connect, the two opposing portions such that the two opposing portions are prevented from moving away from one another. In other words, the fastening means may be configured to tension-resistantly connect the two opposing portions of the medial section. Accordingly, in a released state of the fastening means, the two opposing portions of the medial section are movable relative to one another in a circumferential direction, wherein in a fastened state of the fastening means, two opposing portions of the medial section are prevented from being moved relative to one another, in particular away from and/or towards one another. Further, the footwear may be designed such that the fastening means is configured to be fastened or released independently from releasing or locking the relative translational movement between the tension element and the adjustment unit. In this way, decoupled adjustment of the adjustment mechanism and the adjustable medial section of the upper may be achieved.

Specifically, the fastening means of the medial section may be constituted by at least one lace which is connected to the two opposing portions of the medial section via correspondingly designed lace eyelets. In this configuration, the fastened state of the fastening means may be realized by tying the at least one lace to the lace eyelets, e.g. by means of a shoe-tying knot.

Alternatively or additionally, the fastening means may be constituted by an elastic band which is spanned between the two opposing portions of the medial section. Further, the fastening means may be constituted by a Velcro connection for releasably coupling the two opposing portions of the medial section to one another.

In a further development, the footwear may be designed such that, in the fastened state of the footwear in which the adjustment mechanism applies the pulling force to the toe strap, the adjustment mechanism may be subjected to a further pulling force counteracting the pulling force applied to the toe strap. In this way, an equilibrium of forces at the adjustment mechanism, i.e. the adjustment unit may be provided so as to hold the adjustment mechanism, i.e. the adjustment unit, into position. In this configuration, the further pulling force may be directed from the adjustment mechanism via the medial section into the sole. Optionally, the further pulling force may be directed from the adjustment mechanism via the medial section into the sole such that a tensile force is exerted to the fastening means. Further, this tensile force applied to the medial section, i.e. the fastening means, may induce or cause an elongation of the medial section in its circumferential length.

According to one configuration, the medial section may be constituted by a strap band and a Velcro connection having a first end fastened to the lateral section, in particular to a lower surface thereof, and a correspondingly designed second end fastened to the strap band.

Alternatively or additionally, the adjustment mechanism may comprise a Bowden cable for force-fittingly connecting the adjustment unit to the toe strap, wherein the Bowden cable is constituted by the tension element and a pressure-resistant sleeve in which the tension element is guided. The pressure-resistant sleeve may be, at least partly, constituted by the channel provided through the sole. Specifically, in one configuration, the Bowden cable may be provided such that the pressure-resistant sleeve is connected, i.e. directly connected, to the adjustment unit. In other words, the pressure-resistant sleeve may be provided to extend from the adjustment unit. In this way, a counter force of the pulling force, i.e. a tension force which counteracts the pulling force, may be directed from the adjustment unit into or to the pressure-resistant sleeve. Accordingly, it may be prevented that the counterforce of the pulling force is directed via the medial section into the sole. By such a configuration, the adjustment of the pulling force may be even more effectively decoupled from the adjustment of the circumferential length of the medial section.

BRIEF DESCRIPTION OF THE DRAWINGS

The present disclosure will be more readily appreciated by reference to the following detailed description when being considered in connection with the accompanying drawings in which.

DETAILED DESCRIPTION

In the following, exemplary embodiments will be explained in more detail with reference to the accompanying figures. In the Figures, like elements are denoted by identical reference numerals and repeated description thereof may be omitted in order to avoid redundancies.

In the present disclosure, as is common in anatomy, a reference system is used that is centered on the midline of the wearer's body to indicate position and direction of individual components of the proposed footwear in a state in which the footwear is fastened to a wearer's foot. Accordingly, the term "medial" refers to a direction or side of the footwear pointing towards a medial plane of a wearer's body, i.e. a body of a person who wears the footwear. In anatomy, the term "medial plane", also referred to as "mid-sagittal plane", generally refers to an anatomical plane which divides the body into two bilaterally symmetric parts, i.e. passing through body's midline structures. Accordingly, when describing one of a pair of footwear, i.e. fastened to one of the wearer's foot, the term "in the medial direction" means in a direction of the respective other footwear, i.e. fastened to the other foot of the wearer. To that end, the term "lateral" refers to a direction or side of the footwear pointing away from the medial plane of the wearer's body. Accordingly, when describing one of the pair of footwear, i.e. which is fastened to one of the wearer's foot, the term "in the lateral direction" means in a direction which points away of the respective other footwear, i.e. fastened to the other foot of the wearer.

Figure 1:
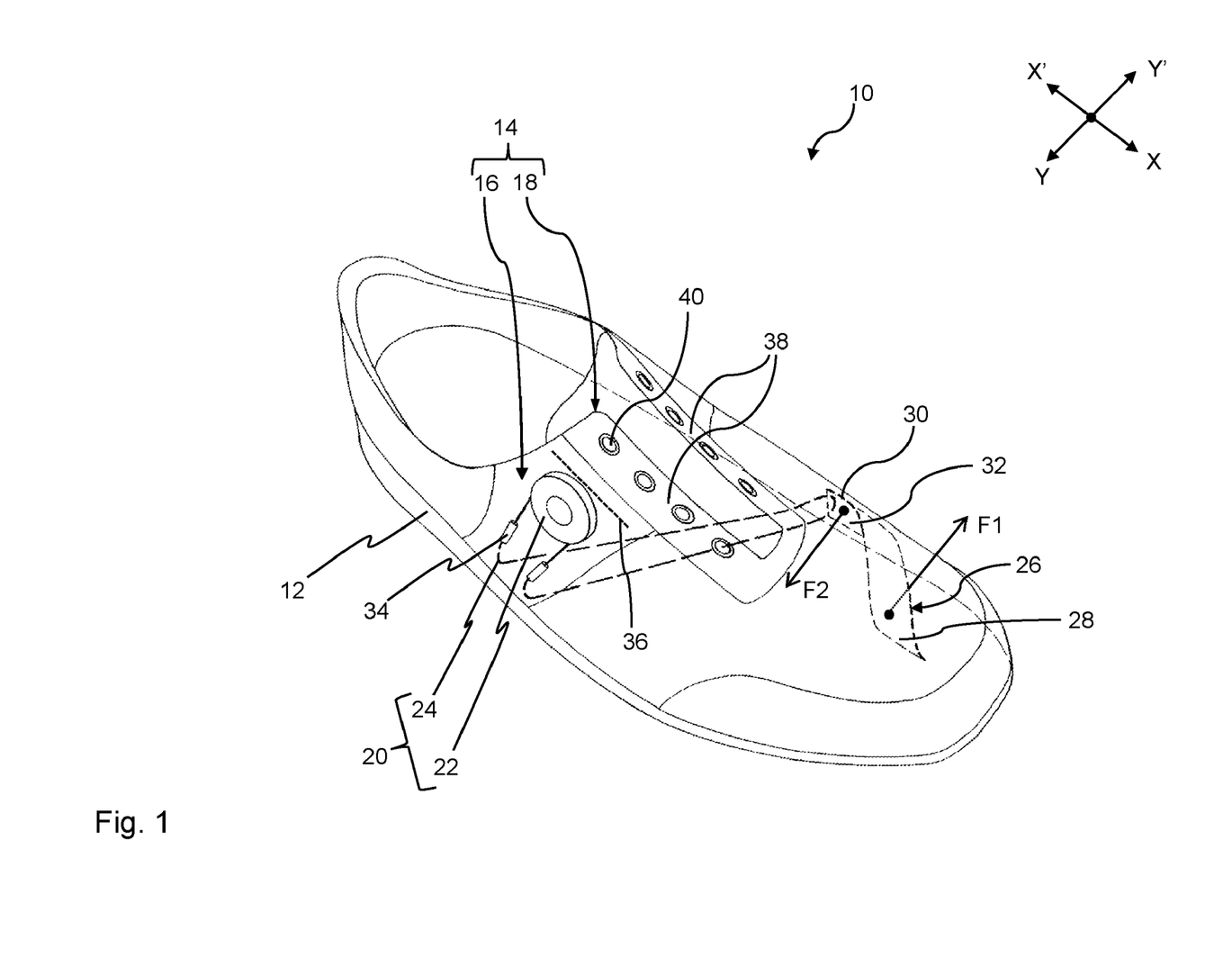
FIG. 1 schematically shows a perspective view of a footwear according to a first configuration which is provided in the form of a closed shoe.

FIG. 1 shows a footwear 10 provided in the form of a closed shoe which is intended to be used for prevention or treatment of a pathological deformity of a wearer's foot (not shown), in particular of a joint connecting a great toe to the foot, also referred to as hallux valgus disease.

The footwear 10 is configured and designed for being releasably fastened to the wearer's foot and, when being fastened to the foot, for providing an intended therapeutic treatment by applying corrective forces to the foot, in particular to the great toe and the great toe joint, as will be described in the following.

The footwear 10 comprises a sole 12 which is configured for receiving a bottom or sole of the foot. The sole 12 is provided with a multi-layer design which is built up by an outsole, a midsole, an insole and an inserted sole which, in an upward direction, are arranged successively one onto the other. Specifically, the inserted sole may be releasably received within the sole 12 so as to be interchangeable.

Further, the footwear 10 comprises an upper 14 which is fixed to the sole 12 and configured to hold the foot within the footwear 10, i.e. in a desired position and orientation relative to the footwear 10. In other words, the upper 14 is configured for being fastened to a metatarsus region of the foot. As can be gathered from FIG. 1, the upper 14 comprises a lateral section 16 and a medial section 18.

The lateral section 16 and the medial section 18 refer to distinct and delimited sections of the upper 14, wherein the lateral section 16 extends from the medial section 18 in a lateral direction Y and the medial section 18 extends from the lateral section 16 in an opposed medial direction Y'.

In the shown configuration, the lateral section 16 and the medial section 18 of the upper 14 are fixed to the sole 12. Specifically, a lateral end of the lateral section 16 of the upper 14 is fixed to a lateral side of the sole 12 and a medial end of the medial section 18 of the upper 14 is fixed to a medial side of the sole 12.

The lateral section 16 carries an adjustment mechanism 20 of the footwear 10 which comprises an adjustment unit 22 and a tension element 24. Specifically, the adjustment mechanism 20 is partly arranged on and within the lateral section 16 of the upper 14 such that the tension element 24 is guided to the lateral side of the footwear 10 as can be gathered from FIG. 1. Specifically, the tension element 24 is provided in the form of a wire which, at one end, is pulled into the adjustment unit 22 and, at the other end, is connected to a toe strap 26 configured for being fastened to the great toe of the foot. Specifically, the footwear 10 is provided such that the tension element 24 is releasably coupled to the toe strap 26. The adjustment mechanism 20 is configured for variably adjusting a pulling force applied to the toe strap 26 which, in the fastened state of the footwear 10, is translated into a corrective force acting upon the great toe and the great toe joint.

The toe strap 26, at least partially, is arranged within the upper 14 and provided such that it is movable relative to the upper 14. In the fastened state of the footwear 10, the toe strap 26 is designed and configured to hold and fix the great toe in a predefined position within the footwear 10, i.e. relative to the sole 12.

Specifically, the toe strap 26 comprises a first end 28 which is firmly fixed to the sole 12 such that, in the fastened state of the footwear 10, the first end 28 of the toe strap 26 is arranged between the great toe and the second toe of the foot. In the shown configuration, the first end 28 of the toe strap 26 protrudes into the sole 12 and is arranged between two layers of the sole 12, for example between the insole and the midsole. Opposed to the first end 28, the toe strap 26 further comprises a second end 30 which, in a forward direction X of the footwear 10 and in the lateral direction Y, is arranged before the first end 28. The second end 30 of the toe strap 26 is releasably coupled to the connecting element 24, thereby enabling that the inserted sole can be exchanged.

As can be gathered from FIG. 1, the toe strap 26 is provided within an elongated and flat shape, wherein its first end 28 is arranged in parallel to the forward direction X of the footwear 10. Further, the toe strap 26 is configured and designed such that, in the fastened state of the footwear 10, it is arranged circumferentially around the great toe such that a wrap length of the toe strap 26 around the great toe is adjustable by applying the pulling force to the toe strap 26 via the tension element 24. More specifically, the toe strap 26 is configured for being spanned around the great toe such that the toe strap 26 extends along an outer surface of the foot from a lateral side of the great toe to a medial side of the great toe and the great toe joint. Accordingly, in the fastened state of the footwear, the toe strap 26 extends backwardly, i.e. along a backward direction X' of the footwear, and medially, i.e. along a medial direction Y' of the footwear, inclined along the outer surface of the great toe. By such a configuration, the great toe is prevented from being subjected to a rotational movement upon applying the pulling force to the toe strap 26.

The toe strap 26 is provided with a seat surface 32 which is configured to, in the fastened state of the footwear 10, fit tightly against the outer surface of the foot. Specifically, the seat surface 32 comprises a first effective surface provided in the region of the first end 28 of the toe strap 26 which tightly fits against the lateral side of the great toe and a second effective surface provided in the region of the second end 30 of the toe strap 26 which fits against the medial side of the great toe and the great toe joint. By such a configuration, upon applying the pulling force to the toe strap 26, the first effective surface applies a first corrective force F1 to the lateral side of the great toe and the second effective surface applies a second corrective force F2 to the medial side of the great toe joint. In this way, both the great toe and the great toe joint are subjected to a corrective therapeutic force which forces them into an anatomically desired or correct position thereby providing an effective therapeutic treatment of hallux valgus diseases.

For purposefully translating the pulling force into the above described corrective forces, the adjustment mechanism is provided such that the tension element 24 is guided through the sole 12 in a width direction thereof so as to be guided to the medial side of the footwear 10 to be connected to the toe strap 26. Specifically, in this configuration, for being capable of applying the pulling force to the toe strap 26, the tension element 24 is movably supported and guided within the footwear 10, in particular within the lateral section 16 of the upper 14 and the sole 12. For doing so, the footwear 10 is provided with a channel 34 which extends subsequently through the lateral section 16 of the upper 14 and the sole 12. By such a configuration, the adjustment mechanism 20 and the lateral section 16 of the upper 14 are designed such that the tension element 24 is directed into the sole 12 from a lateral side of the footwear 10. Further, the channel 34 supports and guides the tension element 24 in the lateral section 16 of the upper 14 and the sole 12 such that the tension element 24 is translationally movable relative to the lateral section 16 and the sole 12 along a longitudinal axis of the tension element 24 and accordingly along a longitudinal axis of the channel 34. In an alternative configuration, the second end 30 of the toe strap 26 may be configured to protrude into the channel 34 so as to be guided therein and translationally movable relative thereto.

Specifically, the channel 34 may be provided such that the channel 34 and accordingly the tension element 24 are guided through the outsole or between the outsole and insole or between the insole and the inserted sole of the sole 12.

Furthermore, in the shown configuration, the channel 34 is designed such that an medial opening (not shown) thereof is arranged to open into an inner space of the upper 14 such that the medial end of the tension element 24 and the second end 30 of the toe strap 24 are arranged within the inner space of the upper 14. Alternatively, the channel 34 may be designed such that the medial opening thereof is arranged at an outer surface of the sole 12 such that the medial end of the tension element 24 and a second end 30 of the toe strap 24 are arranged on an outer surface of the upper 14. In this configuration, a front region of the footwear 10, the upper 14 may be provided with a through opening through which the second end 30 of the toe strap 26 is pulled so as to be arranged onto the outer surface of the upper 14, where it is connected to the tension element.

For actuating the tension element 24, the adjustment mechanism 20 is equipped with the adjustment unit 22. The adjustment mechanism 20 is provided such that the tension element 24 is translationally moved relative to the adjustment unit 22, i.e. along its longitudinal axis, so as to variedly adjust the pulling force applied to the toe strap 26. For doing so, the adjustment unit 22 is configured to selectively release and lock a relative translational movement between the tension element 24 and the adjustment unit 22 along the longitudinal axis of the tension element 24 so as to variedly adjust and set the pulling force applied to the toe strap 26.

In the shown configuration, the adjustment unit 22 is provided in the form of a rotary knob which is configured to translate a rotational movement thereof into a translational movement of the tension element 24 relative to the adjustment unit 22. In other words, upon being rotatably actuated by a user, the adjustment unit 22 causes translational movement of the tension element 24 so as to adjust the pulling force acting upon the pulse strap 26. Specifically, the adjustment unit 22 is configured such that a rotational movement thereof into a first direction causes tightening of the tension element 24 and a rotational movement into a second opposed direction causes untightening of the tension element 24, wherein tightening of the tension element 24 is performed by pulling or retracting the tension element 24 into the adjustment unit 22 and untightening is performed by pulling the tension element out of the adjustment unit 22. In a state, in which the adjustment unit 22 is not actuated by the user, i.e. is not rotationally actuated, the adjustment unit 22 is configured to lock relative movement between the tension element 24 and the adjustment unit 22. In other words, in this state, the tension element 24 is neither pulled in nor out of the adjustment unit 22.

As set forth above, the medial section 18 refers to a part of the upper 14 which is delimited from the lateral section 16 as indicated by a dashed line 36 in FIG. 1. Specifically, the medial section 18 is provided so as to be arranged adjacent to or spaced apart from the adjustment mechanism 20. In other words, the medial section 18 extends from the adjustment mechanism 20, i.e. from the dashed line 36, in the medial direction Y' to the medial side of the footwear 10.

The medial section 18 of the upper is designed such that it is adjustable, i.e. variably adjustable in its circumferential length. For doing so, the medial section 18 is provided with an intermitted section along the circumferential direction. This intermitted section is constituted by two opposing portions 38 which face one another and which are movable relative to one another in the circumferential direction. In other words, upon increasing or decreasing a distance between the two opposing portions 38 of the medial section 18, the circumferential length of the upper 14, i.e. its medial section 18, can be increased or decreased. The medial section is configured such that it is adjustable in its circumferential length independently from an actuation of the adjustment mechanism 20.

For adjusting a desired circumferential length of the upper 14, a fastening means in the form of laces (not shown) and correspondingly designed lace eyelets 40 are provided which are configured to tension-resistantly connect the two opposing portions such that the two opposing portions are prevented from moving away from one another in the circumferential direction. In other words, the fastening means of the medial section 18 is constituted by at least one lace which is connected to the two opposing portions of the medial section via the correspondingly designed lace eyelets 40. In this configuration, a fastened state of the fastening means may be set by tying the at least one lace to the lace eyelets 40, e.g. by means of a shoe-tying knot, wherein a released state of the fastening means for allowing adjustment of circumferential length of the medial section 18 is provided by releasing or untying the laces.

By such a configuration, the footwear 10 is designed such that the fastening means is configured to be fastened or released independently from releasing or locking the relative translational movement between the tension element 24 and the adjustment unit 22.

According to an alternative configuration, the adjustment mechanism may comprise a Bowden cable for force-fittingly connecting the adjustment unit to the toaster 24. In this configuration, the Bowden cable is constituted by the tension element 24 and a pressure-resistance sleeve in which the tension element is guided. Specifically, the pressure-resistance sleeve may be directly or pressure-resistantly connected to the adjustment unit 22.

Figure 2:
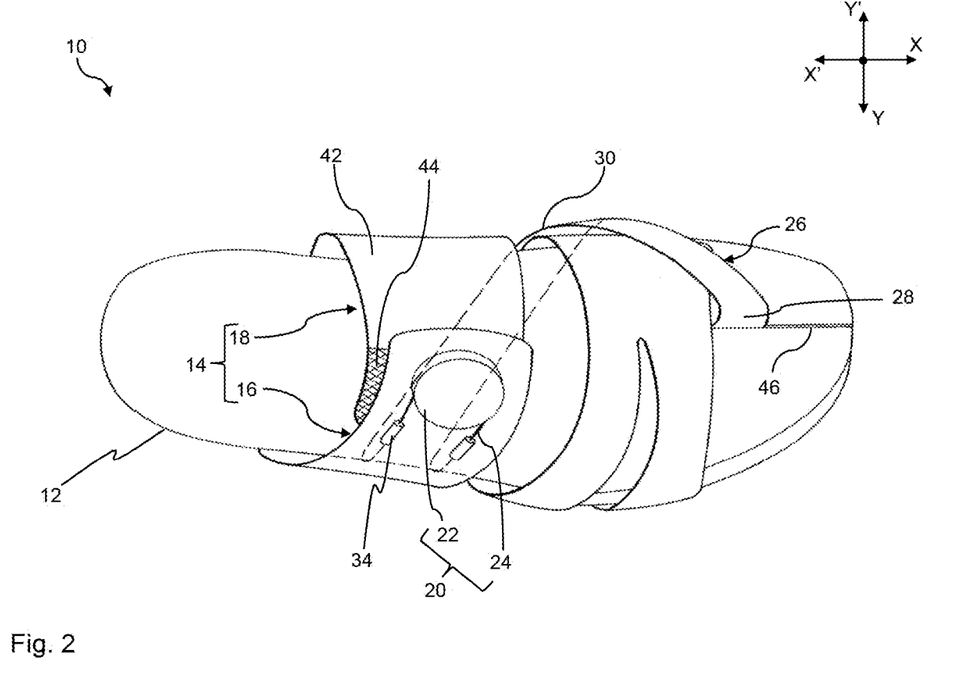
FIG. 2 schematically shows a top view of a footwear according to a second configuration which is provided in the form of a sandal.

FIG. 2 shows another configuration of the footwear 10 which is provided in the form of an open shoe, in particular a sandal. Compared to the configuration depicted in FIG. 1, the footwear 10 further differs by the configuration of the medial section 18 of the upper 14. Specifically, in the configuration depicted in FIG. 2, the medial section 18 is constituted by a strap band 42 and a Velcro connection 44. More specifically, the Velcro connection 44 has a first end fastened to the lateral section, in particular a lower surface of the lateral section 16, and a correspondingly designed second end fastened to the strap band 42, in particular an upper surface thereof. By being provided with the Velcro connection 44, the medial section 18 of the upper 14 can be selectively engaged and disengaged so as to allow adjustment of the circumferential length of the medial section 16 of the upper 14.

To that end, the inserted sole, i.e. the upper layer of the sole 12, is provided with an open slot 46 extending through its thickness direction and from the first end 28 of the toe strap 26 to a forward end of the sole 12. By such a configuration, the inserted sole 12 may be exchanged without the decoupling the tension element 24 from the toe strap 26, in particular from its second end 30.

It will be obvious for a person skilled in the art that these embodiments and items only depict examples of a plurality of possibilities. Hence, the embodiments shown here should not be understood to form a limitation of these features and configurations. Any possible combination and configuration of the described features can be chosen according to the scope of the invention.

LIST OF REFERENCE NUMERALS

10 footwear
12 sole
14 upper
16 lateral section
18 medial section
20 adjustment mechanism
22 adjustment unit
24 tension element
26 toe strap
28 first end of the toe strap
30 second end of the toe strap
32 seat surface
34 channel
36 boundary line
38 opposing portion of the medial section
40 lace eyelets
42 strap band
44 Velcro connection
46 open slot

The invention claimed is:

1. A footwear for preventing or treating a pathological deformity of a wearer's foot, in particular of a joint connecting a great toe to the foot, comprising;
a toe strap configured for being fastened to the great toe,
an upper configured for being fastened to a metatarsus region of the foot and comprising a lateral section and a medial section, and
an adjustment mechanism comprising a tension element coupled to the toe strap and configured for variably adjusting a pulling force applied to the toe strap which, in a fastened state in which the footwear is fastened to the foot, is translated into a corrective force acting upon at least one of the joint and the great toe, wherein
the adjustment mechanism is at least partially arranged in or on the lateral section of the upper such that the tension element is guided to a lateral side of the footwear,
the medial section of the upper extends from the adjustment mechanism in a medial direction to a medial side of the footwear and is adjustable in its circumferential length, and
the medial section is configured such that it is adjustable in its circumferential length independently from an actuation of the adjustment mechanism.

2. The footwear according to claim 1, further comprising a sole to which at least one of a lateral end of the lateral section and a medial end of the medial section is fastened.

3. The footwear according to claim 1, wherein the toe strap comprises a first end fastened to the sole of the footwear and an opposing second end coupled to the tension element of the adjustment mechanism, wherein the toe strap is configured to be arranged circumferentially around the great toe such that, in the fastened state of the footwear, a wrap length of the toe strap around the great toe is adjustable by applying the pulling force to the toe strap.

4. The footwear according to claim 1, wherein the toe strap is configured for being spanned around the great toe such that the toe strap extends along an outer surface of the foot from a lateral side of the great toe to a medial side of the great toe and/or the joint.

5. The footwear according to claim 2, wherein the adjustment mechanism and the lateral section are designed such that the tension element is guided into the sole of the footwear.

6. The footwear according to claim 1, wherein the tension element is supported or guided in the lateral section of the upper such that the tension element is translationally movable relative to the lateral section along a longitudinal axis of the tension element.

7. The footwear according to claim 1, wherein the sole is provided with a channel configured to support or guide the tension element and/or the toe strap such that the tension element and/or the strap are/is translationally movable relative to the sole along a longitudinal axis of the channel.

8. The footwear according to claim 2, wherein the sole is built up of multiple sole layers, and wherein the tension element is guided through an outsole or between the outsole and an insole or between the insole and an inserted sole.

9. The footwear according to claim 1, wherein the medial section of the upper is arranged adjacent to or spaced apart from the adjustment mechanism.

10. The footwear according to claim 1, wherein the adjustment mechanism further comprises an adjustment unit which is configured to selectively release or lock a relative translational movement between the tension element and the adjustment unit along the longitudinal axis of the tension element so as to variedly adjust and set the pulling force applied to the toe strap.

11. The footwear according to claim 10, wherein the medial section comprises a fastening means configured to tension-resistantly connect two opposing portions of the medial section which, in a released state of the fastening means, are movable relative to one another in a circumferential direction, and wherein the fastening means is configured to be fastened and/or released independently from releasing and/or locking the relative translational movement between the tension element and the adjustment unit.

12. The footwear according to claim 11, which is designed such that, in the fastened state of the footwear in which the adjustment mechanism applies the pulling force to the toe strap, the adjustment mechanism is subjected to a further pulling force counteracting the pulling force applied to the toe strap, wherein the further pulling force is directed from the adjustment mechanism via the medial section into the sole such that a tensile force is exerted to the fastening means.

13. The footwear according to claim 1, wherein the adjustment mechanism comprises a Bowden cable for force-fittingly connecting the adjustment unit to the toe strap, wherein the Bowden cable is constituted by the tension element and a pressure-resistant sleeve in which the tension element is guided.

14. The footwear according to claim 1, wherein the medial section is constituted by a strap band and a hook and loop fastener connection having a first end fastened to the lateral section and a correspondingly designed second end fastened to the strap band.

15. The footwear according to claim 2, wherein the toe strap comprises a first end fastened to the sole of the footwear and an opposing second end coupled to the tension element of the adjustment mechanism, wherein the toe strap is configured to be arranged circumferentially around the great toe such that, in the fastened state of the footwear, a wrap length of the toe strap around the great toe is adjustable by applying the pulling force to the toe strap.

16. The footwear according to claim 15, wherein the toe strap is configured for being spanned around the great toe such that the toe strap extends along an outer surface of the foot from a lateral side of the great toe to a medial side of the great toe and/or the joint.

17. The footwear according to claim 16, wherein the adjustment mechanism and the lateral section are designed such that the tension element is guided into the sole of the footwear.

18. The footwear according to claim 17, wherein the tension element is supported or guided in the lateral section of the upper such that the tension element is translationally movable relative to the lateral section along a longitudinal axis of the tension element.

19. The footwear according to claim 1, wherein the sole is provided with a channel configured to support or guide the tension element and/or the toe strap such that the tension element and/or the strap are/is translationally movable relative to the sole along a longitudinal axis of the channel.

* * * * *